(12) United States Patent
Taylor

(10) Patent No.: US 9,744,015 B2
(45) Date of Patent: Aug. 29, 2017

(54) URETHRA CUFF INCLUDING TUBE

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/881,173

(22) Filed: Oct. 13, 2015

(65) Prior Publication Data

US 2016/0135938 A1 May 19, 2016

Related U.S. Application Data

(60) Provisional application No. 62/080,417, filed on Nov. 17, 2014.

(51) Int. Cl.
*A61F 2/00* (2006.01)

(52) U.S. Cl.
CPC ...... *A61F 2/004* (2013.01); *A61F 2230/0069* (2013.01); *A61F 2230/0091* (2013.01)

(58) Field of Classification Search
CPC ....... A61B 5/42; A61B 5/6876; A61B 5/6884; A61B 5/02233; A61B 17/12009; A61B 90/06; A61B 2017/00557; Y10S 128/25
USPC .............................. 600/29–31, 40
See application file for complete search history.

(56) References Cited

U.S. PATENT DOCUMENTS

| | | |
|---|---|---|
| 3,744,063 A | 7/1973 | McWhorter et al. |
| 4,063,548 A | 12/1977 | Klatt et al. |
| 4,191,196 A | 3/1980 | Bradley et al. |
| 4,222,377 A * | 9/1980 | Burton ............... A61F 2/004 |
| | | 128/DIG. 25 |
| 4,412,530 A | 11/1983 | Burton |
| 4,428,365 A | 1/1984 | Hakky |
| 4,556,050 A | 12/1985 | Hodgson et al. |
| 4,878,889 A | 11/1989 | Polyak |
| 4,881,939 A * | 11/1989 | Newman ........... A61B 5/02233 |
| | | 128/DIG. 25 |
| 4,909,785 A | 3/1990 | Burton et al. |
| 4,932,956 A | 6/1990 | Reddy et al. |
| 4,932,958 A | 6/1990 | Reddy et al. |
| 4,994,020 A | 2/1991 | Polyak |
| 5,078,720 A | 1/1992 | Burton et al. |
| 5,181,911 A * | 1/1993 | Shturman ......... A61M 25/104 |
| | | 604/103.07 |
| 5,335,669 A | 8/1994 | Tihon et al. |
| 5,356,423 A | 10/1994 | Tihon et al. |
| 5,496,271 A | 3/1996 | Burton et al. |
| 5,499,994 A | 3/1996 | Tihon et al. |
| 5,518,504 A | 5/1996 | Polyak |

(Continued)

OTHER PUBLICATIONS

Americal Medical Systems, Operating Room Manual, USA 2004.

*Primary Examiner* — Samuel Gilbert
(74) *Attorney, Agent, or Firm* — Coloplast Corp., Coloplast A/S; Nick Baumann

(57) ABSTRACT

An artificial urinary sphincter (AUS) system that includes a reservoir to hold a fluid, a cuff that includes a pre-shaped spiral tube to be wrapped around a urethra, and a control device to be fluidically coupled to the reservoir and the cuff. The control device regulates transfer of the fluid between the reservoir and the cuff. The cuff receives and dispatches the fluid to expand and contract the pre-shaped spiral tube and to coapt the urethra for continence and open the urethra for voiding.

13 Claims, 10 Drawing Sheets

(56) References Cited

U.S. PATENT DOCUMENTS

| | | | |
|---|---|---|---|
| 5,562,598 A * | 10/1996 | Whalen | A61F 2/004 128/DIG. 25 |
| 5,720,415 A | 2/1998 | Morningstar | |
| 5,895,356 A | 4/1999 | Andrus et al. | |
| 6,382,214 B1 | 5/2002 | Raz et al. | |
| 6,612,977 B2 | 9/2003 | Staskin et al. | |
| 6,616,653 B2 | 9/2003 | Beyar et al. | |
| 6,652,450 B2 | 11/2003 | Neisz et al. | |
| 6,802,807 B2 | 10/2004 | Anderson et al. | |
| 6,971,986 B2 | 12/2005 | Staskin et al. | |
| 7,015,253 B2 | 3/2006 | Escandon et al. | |
| 7,048,682 B2 | 5/2006 | Neisz et al. | |
| 7,083,568 B2 | 8/2006 | Neisz et al. | |
| 7,267,645 B2 | 9/2007 | Anderson et al. | |
| 7,291,104 B2 | 11/2007 | Neisz et al. | |
| 7,315,762 B2 | 1/2008 | Mosher et al. | |
| 2003/0028076 A1 | 2/2003 | Kujava et al. | |
| 2005/0059929 A1 | 3/2005 | Bolmsjo et al. | |
| 2009/0240100 A1 | 9/2009 | Forsell | |
| 2012/0147759 A1 | 6/2012 | Ratnakar et al. | |
| 2013/0019871 A1 * | 1/2013 | Nemirovsky | A61M 16/0495 128/207.15 |

* cited by examiner

URETHRA CUFF INCLUDING TUBE

BACKGROUND

Urinary incontinence affects many people and is a worldwide health issue. Published research indicates that urinary incontinence presents a substantial social and economic burden worldwide, affecting up to a mean of about 16% of the global population.

Urinary incontinence in women can be associated with a prolapse of one or more pelvic organs, which can arise from child birth or a weakness in the tissues/muscle of the pelvic floor. Urinary incontinence in men can arise after surgical treatment of the prostate gland, which treatment can include removal or weakening of the prostatic sphincter of the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

Some embodiments of the disclosure provide an artificial urinary sphincter (AUS) system that includes a reservoir to hold a fluid, a cuff that includes a pre-shaped spiral tube to be wrapped around a urethra, and a control device to be fluidically coupled to the reservoir and the cuff. The control device regulates transfer of the fluid between the reservoir and the cuff. The cuff receives and dispatches the fluid to expand and contract the pre-shaped spiral tube and to coapt the urethra for continence and open the urethra for voiding.

Some embodiments of the disclosure provide an AUS system that includes a reservoir to hold a fluid, a cuff that includes kink resistant tubing to be wrapped around a urethra, and a control device to be fluidically coupled to the reservoir and the cuff. The control device regulates movement of the fluid between the reservoir and the cuff. The cuff receives and dispatches the fluid to expand and contract the kink resistant tubing and to coapt the urethra for continence and open the urethra for voiding While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
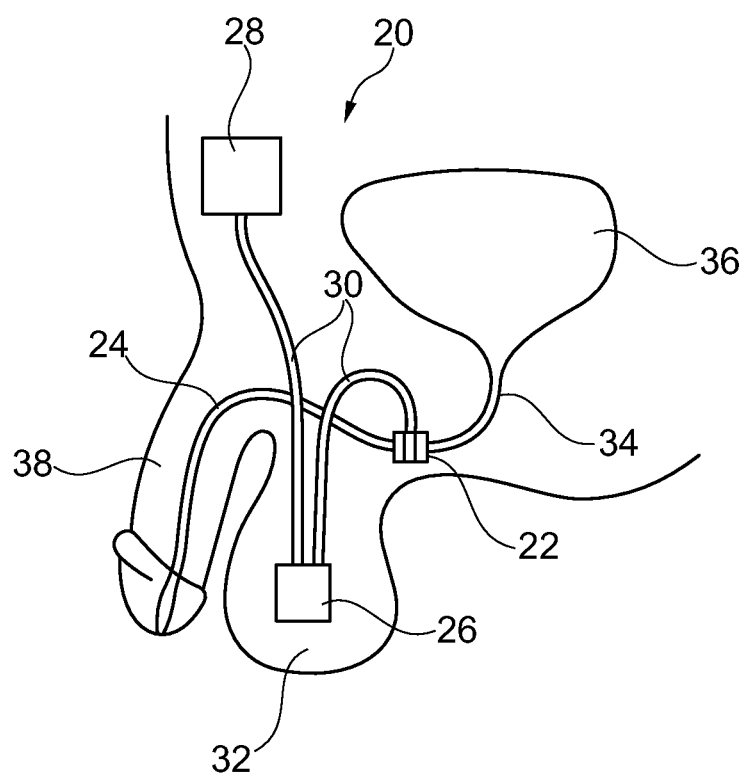
FIG. 1 is a diagram illustrating one embodiment of an AUS system implanted in the environment of the male urogenital region.

In the following Detailed Description, reference is made to the accompanying drawings, which form a part hereof, and in which is shown by way of illustration embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the disclosure. The following detailed description, therefore, is not to be taken in a limiting sense.

The features of the various exemplary embodiments described in this disclosure may be combined with each other ("mixed and matched"), unless specifically noted otherwise.

End means endmost. A distal end is the furthest endmost location of a distal portion of a thing being described, whereas a proximal end is the nearest endmost location of a proximal portion of the thing being described. The portion next to or adjacent to an end is an end portion. Also, soft tissue includes dermal tissue, sub-dermal tissue, ligaments, tendons, or membranes but does not include bone.

Artificial urinary sphincters have proved useful in the treatment of urinary incontinence. An AUS is implanted around the urethra and operable to selectively coapt the lumen of the urethra to allow the user to shift the artificial sphincter from an open state that allows urine to pass to a closed state that provides the user with continence.

One urinary control system that has found favor with the medical community includes three components cooperatively attached with tubing. The three components include an occlusive cuff, a control pump, and a pressure-regulating balloon reservoir. The cuff is implanted around the urethra, the control pump is implanted in the scrotum of a male user, and the pressure-regulating balloon reservoir is implanted in the prevesical space. The three components are filled with a liquid to provide a liquid-filled closed system that is maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra. The cuff is fabricated from sheets of film that are sealed to provide one or more inflatable cushions. The cuff is provided in a rectangular shape and intended to be placed around the urethra, with the ends of the rectangular cuff secured together. However, observers have noticed that the cuff of this system has a tendency to kink when it inflates, particularly at the junction of where the rectangular balloon cushions are formed into a circular cuff. The location of this kink can wear over time and create a leak in the cuff.

Embodiments described in this disclosure provide an AUS system that includes a cuff that includes a tube to be wrapped around the urethra. In some embodiments, the tube is a pre-shaped spiral tube to be wrapped around the urethra. In some embodiments, the tube includes kink resistant tubing to be wrapped around the urethra.

Embodiments described in this disclosure further include a fluid reservoir that holds a fluid, such as a saline solution, and a control device that is configured to be fluidically coupled to the reservoir and the cuff. The control device regulates movement of the fluid between the reservoir and the cuff, such that the cuff receives and dispatches the fluid to expand and contract the tube. In some embodiments, the tube is inflated to expand and coapt the urethra to maintain continence and deflated to contract and open the urethra for voiding. In some embodiments, the tube is inflated to expand and open the urethra for voiding and deflated to contract and coapt the urethra to maintain continence or prevent incontinence.

The AUS systems described in this disclosure are suited for use in both female patients and male patients, where the cuff is placed around a portion of the urethra. Female patients can have the control device component implanted in one of the labia or an abdominal area. Male patients can have the control device component implanted in the scrotum.

FIG. 1 is a diagram illustrating one embodiment of an AUS system 20 implanted in the environment of the male urogenital region. The AUS system 20 includes a cuff 22 situated around the urethra 24. The AUS system 20 also includes a control device 26 that is fluidically connected to the cuff 22 and to a fluid reservoir 28 via tubing 30, such as kink-resistant tubing.

The cuff 22 includes an elastic tube that is wrapped around or rotated around the urethra 24 and a connector that connects the elastic tube to the control device 26. In some embodiments, the cuff 22 is inflated to expand the elastic tube and coapt or close-off the urethra 24 to prevent incontinence and deflated to contract the elastic tube and open the urethra 24 for voiding. In some embodiments, the cuff 22 is inflated to expand the elastic tube and open the urethra 24 for voiding and deflated to contract the elastic tube and coapt or close-off the urethra 24 to maintain continence.

The control device 26 and the fluid reservoir 28 are operable to inflate and deflate the cuff 22. The fluid reservoir 28 is sized to retain a volume of liquid, such as a saline solution, that can be moved into the cuff 22 to expand the elastic tube.

In some embodiments, the fluid reservoir 28 provides a regulated fluid pressure and the control device 26 includes a control valve that, upon activation, allows the fluid to move from the fluid reservoir 28 into the cuff 22, which expands the cuff 22 to coapt or close-off the urethra 24 and maintain continence. In some of these embodiments, the control device 26 includes a pump bulb that, upon squeezing, moves the fluid from the cuff 22 to the fluid reservoir 28 to deflate the cuff 22, where the bias of the elastic tube in the cuff 22 assists in deflating the cuff 22. The deflated cuff 22 allows the urethra 24 to open for voiding. In some embodiments, the fluid reservoir 28 that provides a regulated fluid pressure, automatically inflates the cuff 22 over time, such as 2 or 3 minutes or less, through a leaky valve arrangement in the control device 26 and the cuff 22, which expands the cuff 22 to coapt or close-off the urethra 24 and prevent incontinence. In some embodiments, other suitable pumps are used, such as electromechanical pumps, electronic pumps, and button-style cavity pumps.

In some embodiments, the fluid reservoir 28 provides a regulated fluid pressure and the control device 26 includes a control valve that, upon activation, allows the fluid to move from the fluid reservoir 28 into the cuff 22. This expands the cuff 22 to allow the urethra 24 to open for voiding. In some of these embodiments, the control device 26 includes a pump bulb that, upon squeezing, moves the fluid from the cuff 22 to the fluid reservoir 28 to deflate the cuff 22, where the bias of the elastic tube in the cuff 22 assists in deflating the cuff 22. The deflated cuff 22 coapts or closes off the urethra 24 to maintain continence. In some embodiments, other suitable pumps are used, such as electromechanical pumps, electronic pumps, and button-style cavity pumps.

In some embodiments, the fluid reservoir 28 does not provide a regulated fluid pressure and the control device 26 includes a pump bulb that, upon squeezing, moves the fluid from the fluid reservoir 28 to the cuff 22. This expands the cuff 22 to coapt or close-off the urethra 24. In some of these embodiments, the control device 26 includes a control valve that, upon activation, allows the fluid to move from the cuff 22 into the fluid reservoir 28, where the bias of the elastic tube in the cuff 22 assists in deflating the cuff 22. This deflates the cuff 22 to allow the urethra 24 to open for voiding. In some embodiments, other suitable pumps are used, such as electromechanical pumps, electronic pumps, and button-style cavity pumps.

In some embodiments, the fluid reservoir 28 does not provide a regulated fluid pressure and the control device 26 includes a pump bulb that, upon squeezing, moves the fluid from the fluid reservoir 28 to the cuff 22. This expands the cuff 22 to allow the urethra 24 to open for voiding. In some of these embodiments, the cuff 22 automatically deflates over time, such as 2 or 3 minutes or less, through a leaky valve arrangement in the control device 26 and the cuff 22, where the bias of the elastic tube in the cuff 22 assists in deflating the cuff 22. The deflated cuff 22 coapts or closes off the urethra 24 to prevent incontinence. In some embodiments, other suitable pumps are used, such as electromechanical pumps, electronic pumps, and button-style cavity pumps.

The control device 26 can be implanted within the scrotum 32, which provides access to the control device 26 by the user. Also, other locations for placement of the control device 26 are acceptable, for example as determined by the gender of the user.

The tubing 30 is provided in a kink resistant form and includes some style of connector that allows segments of the tubing 30 to be attached together after the various components, such as the control device 26 and the fluid reservoir 28, are primed with liquid. The tubing 30 is a thin-walled tube that is attachable between the control device 26 and the fluid reservoir 28, and between the control device 26 and the cuff 22. In one embodiment, the tubing 30 is separate from the control device 26 and separate from the fluid reservoir 28 and connects to these components through a locking mechanism, such as a quick connector or other suitable snap-fit connector.

The cuff 22 is implanted around the bulbous urethra or around the portion of the urethra 24 descending from the bladder neck 34. The cuff 22 is sized to allow placement as close to the bladder 36 as possible (desired by some surgeons), or positioned distal the bladder neck 34 as suitably determined by the attending surgeon. As illustrated in FIG. 1, the cuff 22 is implanted around the urethra 24 at a location where the urethra 24 transitions from a vertical orientation communicating with the bladder 36 to a horizontal orientation extending to the penis 38, which desirably corresponds to the area of the urogenital region associated with an increased level of muscle mass.

Figure 2A:
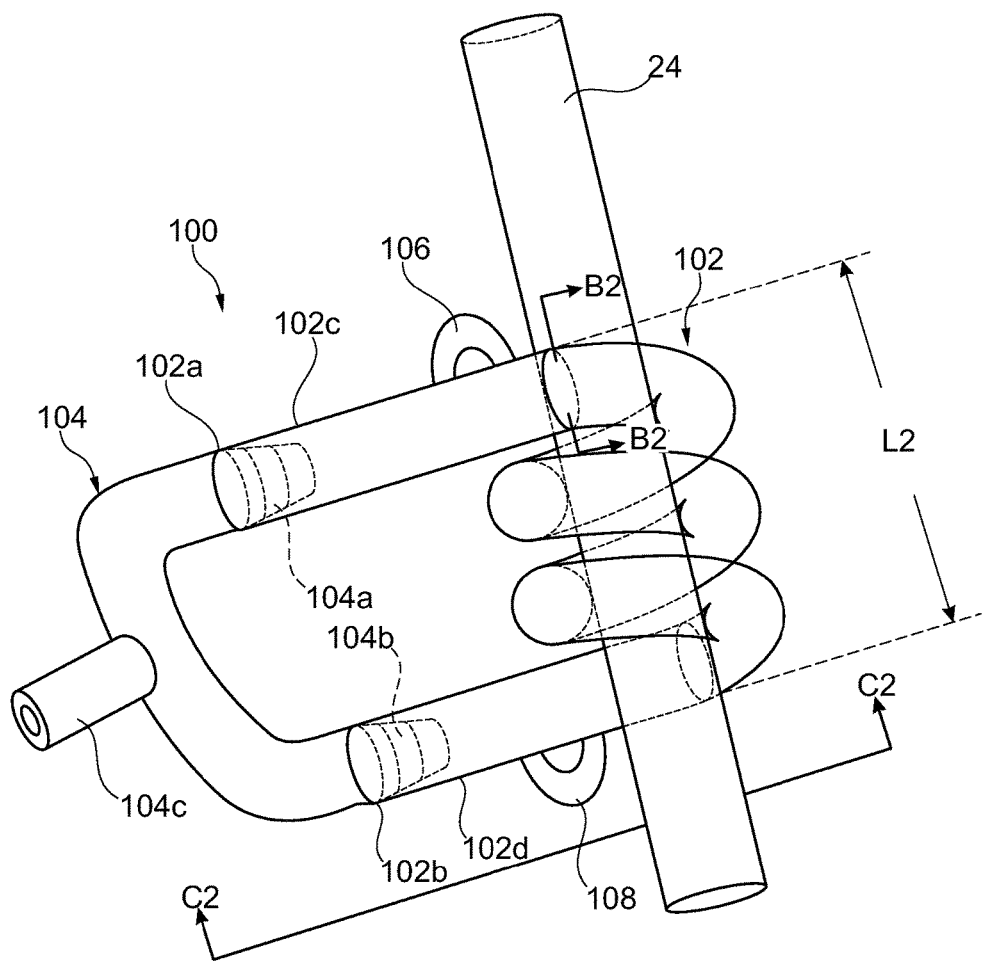
FIG. 2A is a diagram illustrating one embodiment of a cuff, which includes a pre-shaped spiral tube and a connector, on the urethra.

FIG. 2A is a diagram illustrating one embodiment of a cuff 100, which includes a pre-shaped spiral tube 102 and a connector 104, on the urethra 24. In some embodiments, the cuff 100 is similar to the cuff 22 (shown in FIG. 1).

The pre-shaped spiral tube 102 has a first end 102a and a second end 102b, and the connector 104 includes a first connector 104a, a second connector 104b, and a third connector 104c. The first end 102a and a first end portion 102b of the pre-shaped spiral tube 102, which is adjacent the first end 102a, engage the first connector 104a to provide a snug, fluid tight fit. The second end 102b and a second end portion 102d of the pre-shaped spiral tube 102, which is adjacent the second end 102b, engage the second connector 104b to provide a snug, fluid tight fit. The third connector 104c is suitable for attachment to tubing, such as tubing 30 (shown in FIG. 1).

The pre-shaped spiral tube 102 is sized to fit around the urethra 24. The pre-shaped spiral tube 102 is wrapped around the urethra 24 multiple times, such as 2 or 3 or more times, to form annular rings or coils around the urethra 24. The pre-shaped spiral tube 102 is wrapped around the urethra 24 for a length L2 of the urethra 24. In this embodiment, the same force can be used with multiple coils as with a single coil to constrict the urethra 24, but the force is applied over an increased area of the urethra 24, such that the pressure at points along the urethra 24 is decreased. The decreased pressure along the urethra 24 leads to less irritation and less eroding of the urethra 24 under the cuff 100. In some embodiments, the pre-shaped spiral tube 102 is wrapped around the urethra 24 for a length L2 of up to 2 centimeters (cm). In some embodiments, the pre-shaped spiral tube 102 is wrapped around the urethra 24 for a length L2 of less than 1 cm.

In some embodiments, the pre-shaped spiral tube 102 includes eyelets 106 and 108 for securing and anchoring the pre-shaped spiral tube 102 to the tissue of the patient. The eyelets 106 and 108 can be situated at the end portions 102c and 102d, respectively, of the pre-shaped spiral tube 102. The eyelets 106 and 108 are secured or tied to the tissue of the patient to anchor the pre-shaped spiral tube 102 in place and to prevent the coils of the pre-shaped spiral tube 102 from expanding and separating further apart along the length L2 of the urethra 24.

The pre-shaped spiral tube 102 is pre-shaped or pre-formed to fit around the urethra 24, such that the pre-shaped spiral tube 102 does not kink or wrinkle as it is wrapped around the urethra 24. In some embodiments, the pre-shaped spiral tube 102 is pre-shaped or pre-formed into a circular shape to fit around the urethra, such that the pre-shaped spiral tube 102 does not kink or wrinkle as it is wrapped around the urethra 24. In some embodiments, the pre-shaped spiral tube 102 is pre-shaped or pre-formed into an oblong or oval shape to fit around the urethra, such that the pre-shaped spiral tube 102 does not kink or wrinkle as it is wrapped around the urethra 24.

The pre-shaped spiral tube 102 is made out of an elastic material, such that the pre-shaped spiral tube 102 expands upon being filled with fluid. In some embodiments, the pre-shaped spiral tube 102 includes a urethane elastomer. In some embodiments, the pre-shaped spiral tube 102 includes a urethane elastomer having a wall thickness of between 0.25 and 2 millimeters (mm), such as a wall thickness of 0.75 mm. In some embodiments, the pre-shaped spiral tube 102 includes silicone. In some embodiments, the pre-shaped spiral tube 102 includes silicone having a wall thickness of between 1 and 2 mm.

To put the cuff 100 around the urethra 24, one of the first and second ends 102a and 102b of the pre-shaped spiral tube 102 can be slid behind the urethra 24 to emerge from the other side of the urethra 24. The selected end can then be repeatedly wrapped around the urethra 24 by sliding the selected end behind the urethra 24 to twist or rotate the pre-shaped spiral tube 102 onto the urethra 24. After the pre-shaped spiral tube 102 has been wrapped around the urethra 24 multiple times, the first end 102a is connected to the first connector 104a, the second end 102b is connected to the second connector 104b, and tubing, such as tubing 30 (shown in FIG. 1), is connected to the third connector 104c.

In some embodiments, the eyelets 106 and 108 are secured to the tissue of the patient. This prevents the pre-shaped spiral tube 102 from sliding up and down on the urethra 24 and ensures expansion of the pre-shaped spiral tube 102 on the urethra 24 without separating or further separating the coils of the pre-shaped spiral tube 102.

Figure 2B:
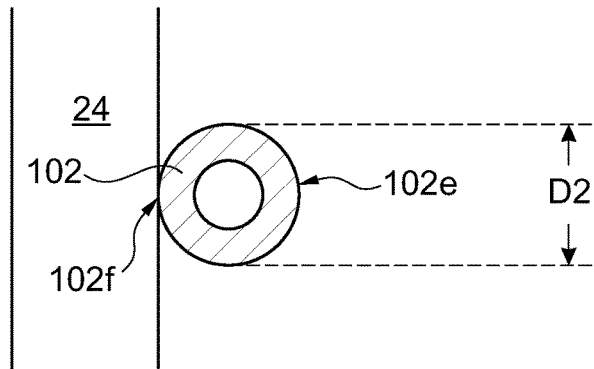
FIG. 2B is a cross-sectional diagram of the pre-shaped spiral tube taken along the line B2-B2 in FIG. 2A.

FIG. 2B is a cross-sectional diagram of the pre-shaped spiral tube 102 and the urethra 24 taken along the line B2-B2 in FIG. 2A. The pre-shaped spiral tube 102 has a circular cross-section and, in some embodiments, the pre-shaped spiral tube 102 has a circular cross-section from the first end 102a to the second end 102b. The pre-shaped spiral tube 102 has an exterior surface 102e that is the outermost portion of the pre-shaped spiral tube 102 and an inner surface 102f that is provided to contact the urethra 24. The exterior surface 102e is opposite of or 180 degrees displaced from the inner surface 102f. In some embodiments, the pre-shaped spiral tube 102 has an outer diameter D2 of between 2 and 9 mm.

Figure 2C:
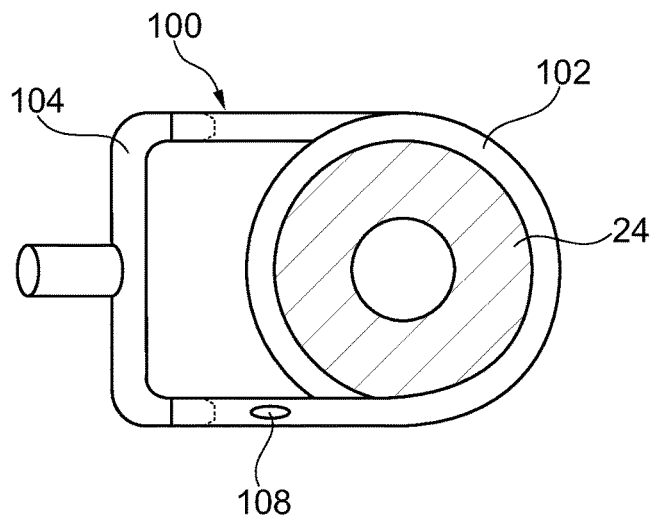
FIG. 2C is a diagram illustrating the pre-shaped spiral tube situated around the urethra, where the pre-shaped spiral tube is deflated and the urethra is open for voiding.
Figure 2D:
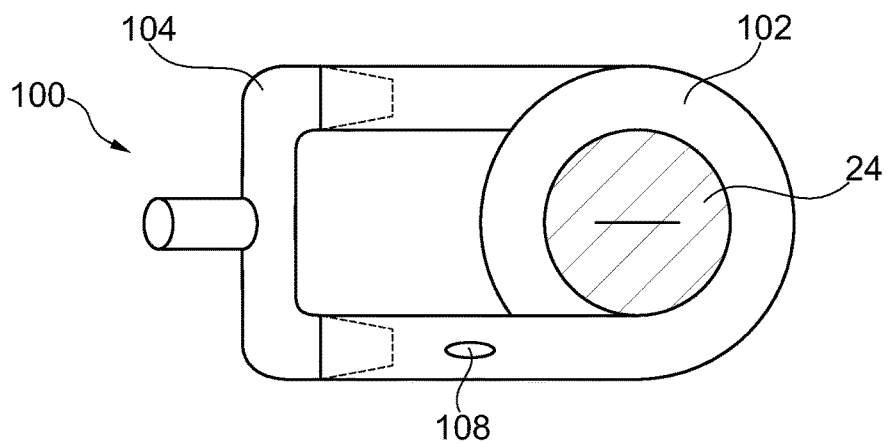
FIG. 2D is a diagram illustrating the pre-shaped spiral tube situated around the urethra, where the pre-shaped spiral tube is inflated and the urethra is closed off to prevent incontinence.

FIGS. 2C and 2D are cross-sectional diagrams taken along the line C2-C2 in FIG. 2A illustrating one embodiment of the cuff 100, which is deflated to contract the pre-shaped spiral tube 102 and open the urethra 24 for voiding and inflated to expand the pre-shaped spiral tube 102 and coapt or close-off the urethra 24 to prevent incontinence. FIG. 2C is a diagram illustrating the pre-shaped spiral tube 102 situated around the urethra 24, where the pre-shaped spiral tube 102 is deflated and the urethra 24 is open for voiding. FIG. 2D is a diagram illustrating the pre-shaped spiral tube 102 situated around the urethra 24, where the pre-shaped spiral tube 102 is inflated and the urethra 24 is closed off to prevent incontinence.

In operation, as described in reference to FIG. 1, a control device such as control device 26 and a fluid reservoir such as fluid reservoir 28 cooperate to move fluid from the fluid reservoir to the pre-shaped spiral tube 102 of the cuff 100. This expands the pre-shaped spiral tube 102 and pinches off or closes the urethra 24 (shown in FIG. 2D). At the appropriate time, the fluid is removed from the pre-shaped spiral tube 102, which relaxes or contracts the pre-shaped spiral tube 102 from around the urethra 24 to allow the urethra 24 to open for voiding (shown in FIG. 2C). The control device and the fluid reservoir further cooperate to move fluid from the fluid reservoir to the pre-shaped spiral tube 102 to expand the pre-shaped spiral tube 102 and close the urethra 24 to prevent incontinence.

Figure 3A:
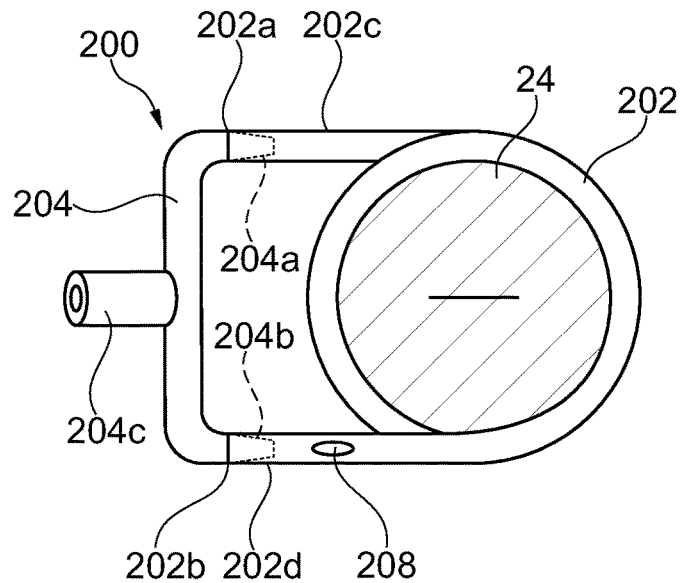
FIG. 3A is a diagram illustrating the pre-shaped spiral tube situated around the urethra, where the pre-shaped spiral tube is deflated and contracted to pinch off or close the urethra to prevent incontinence.
Figure 3B:
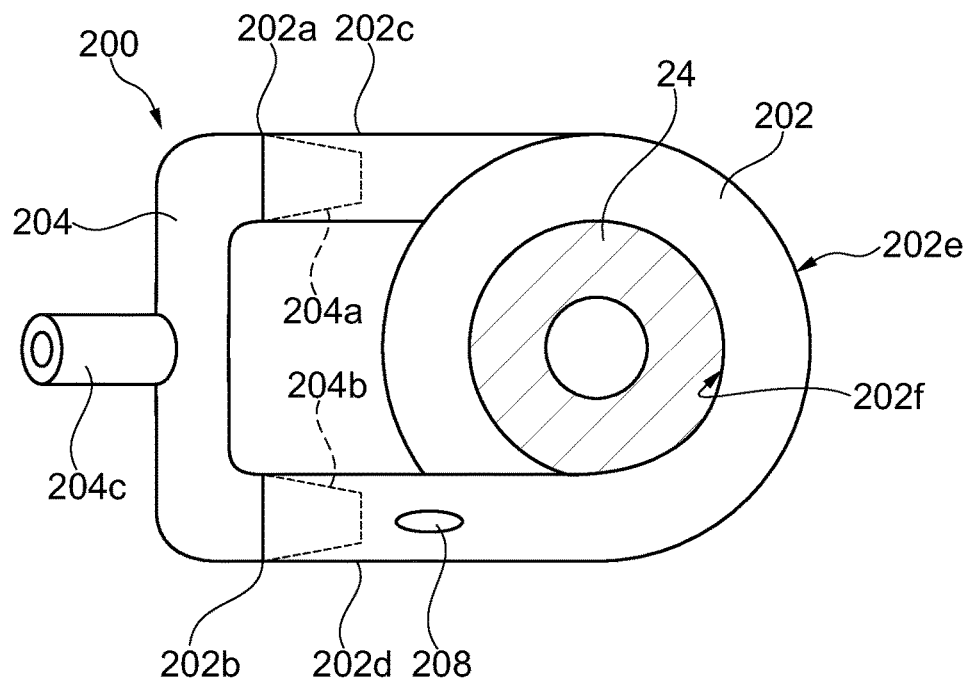
FIG. 3B is a diagram illustrating the pre-shaped spiral tube situated around the urethra, where the pre-shaped spiral tube is inflated and expanded to allow the urethra to open for voiding.

FIGS. 3A and 3B are diagrams illustrating one embodiment of a cuff 200 that is similar to the cuff 100, except the cuff 200 includes a pre-shaped spiral tube 202 that is deflated to contract the pre-shaped spiral tube 202 to close-off the urethra 24 and prevent incontinence, and inflated to expand the pre-shaped spiral tube 202 to allow the urethra 24 to open for voiding. In some embodiments, the cuff 200 is similar to the cuff 22 (shown in FIG. 1).

The cuff 200 includes the pre-shaped spiral tube 202 and a connector 204. The pre-shaped spiral tube 202 has a first end 202a and a second end 202b, and the connector 204 includes a first connector 204a, a second connector 204b, and a third connector 204c. The first end 202a and a first end portion 202c of the pre-shaped spiral tube 202, which is adjacent the first end 202a, engage the first connector 204a to provide a snug, fluid tight fit. The second end 202b and a second end portion 202d of the pre-shaped spiral tube 202, which is adjacent the second end 202b, engage the second connector 204b to provide a snug, fluid tight fit. The third connector 204c is suitable for attachment to tubing, such as tubing 30 (shown in FIG. 1).

The pre-shaped spiral tube 202 is sized to fit around the urethra 24, and similar to the pre-shaped spiral tube 102, the pre-shaped spiral tube 202 is wrapped around the urethra 24 multiple times, such as 2 or 3 or more times, to form annular rings or coils around the urethra 24. The pre-shaped spiral tube 202 is wrapped around the urethra 24 for a length, similar to length L2, along the urethra 24, where the same force can be used with multiple coils as with a single coil to constrict the urethra 24, but the force is applied over an increased area of the urethra 24, such that pressure at points along the urethra 24 is decreased. The decreased pressure along the urethra 24 leads to less irritation and less eroding of the urethra 24 under the cuff 200. In some embodiments, the pre-shaped spiral tube 202 is wrapped around the urethra 24 for a length of up to 2 cm. In some embodiments, the pre-shaped spiral tube 202 is wrapped around the urethra 24 for a length of less than 1 cm.

The pre-shaped spiral tube 202 has a circular cross-section and, in some embodiments, the pre-shaped spiral tube 202 has a circular cross-section from the first end 202a to the second end 202b. The pre-shaped spiral tube 202 has an exterior surface 202e that is the outermost portion of the pre-shaped spiral tube 202 and an inner surface 202f that is provided to contact the urethra 24. The exterior surface 202e is opposite of or 180 degrees displaced from the inner surface 202f. In some embodiments, the pre-shaped spiral tube 202 has an outer diameter, similar to diameter D2, of between 2 and 9 mm.

In some embodiments, the pre-shaped spiral tube 202 includes eyelets, such as eyelet 208, for securing and anchoring the pre-shaped spiral tube 202 to the tissue of the patient. The eyelets can be situated at the end portions 202c and 202d, respectively, of the pre-shaped spiral tube 202 and secured or tied to the tissue of the patient to anchor the pre-shaped spiral tube 202 in place and to prevent the coils of the pre-shaped spiral tube 202 from expanding and separating further apart along the length of the urethra 24.

The pre-shaped spiral tube 202 is pre-shaped or pre-formed to fit around the urethra 24, such that the pre-shaped spiral tube 202 does not kink or wrinkle as it is wrapped around the urethra 24. In some embodiments, the pre-shaped spiral tube 202 is pre-shaped or pre-formed into a circular shape to fit around the urethra, such that the pre-shaped spiral tube 202 does not kink or wrinkle as it is wrapped around the urethra 24. In some embodiments, the pre-shaped spiral tube 202 is pre-shaped or pre-formed into an oblong or oval shape to fit around the urethra, such that the pre-shaped spiral tube 202 does not kink or wrinkle as it is wrapped around the urethra 24.

The pre-shaped spiral tube 202 is made out of an elastic material, such that the pre-shaped spiral tube 202 expands upon being filled with fluid. In some embodiments, the pre-shaped spiral tube 202 includes a urethane elastomer. In some embodiments, the pre-shaped spiral tube 202 includes a urethane elastomer having a wall thickness of between 0.25 and 2 mm, such as a wall thickness of 0.75 mm. In some embodiments, the pre-shaped spiral tube 102 includes silicone. In some embodiments, the pre-shaped spiral tube 202 includes silicone having a wall thickness of between 1 and 2 mm.

The cuff 200 can be put around the urethra 24 similar to the way in which the cuff 100 is put around the urethra 24. Also, in some embodiments, the eyelets are secured to the tissue of the patient to prevent the pre-shaped spiral tube 202 from sliding up and down on the urethra 24 and to ensure expansion of the pre-shaped spiral tube 202 on the urethra without separating or further separating the coils of the pre-shaped spiral tube 202.

FIG. 3A is a diagram illustrating the pre-shaped spiral tube 202 situated around the urethra 24, where the pre-shaped spiral tube 202 is deflated and contracted to pinch or close-off the urethra 24 to prevent incontinence. FIG. 3B is a diagram illustrating the pre-shaped spiral tube 202 situated around the urethra 24, where the pre-shaped spiral tube 202 is inflated and expanded to allow the urethra 24 to open for voiding.

In operation, as described in reference to FIG. 1, a control device such as control device 26 and a fluid reservoir such as fluid reservoir 28 cooperate to move fluid from the fluid reservoir to the pre-shaped spiral tube 202 of the cuff 200. This expands the pre-shaped spiral tube 202 from around the urethra 24 and allows the urethra 24 to open for voiding (shown in FIG. 3B). After some time, the fluid is removed from the pre-shaped spiral tube 202, which contracts the pre-shaped spiral tube 202 to tighten around the urethra 24 and close-off the urethra 24 to prevent incontinence (shown in FIG. 3A).

Figure 4:
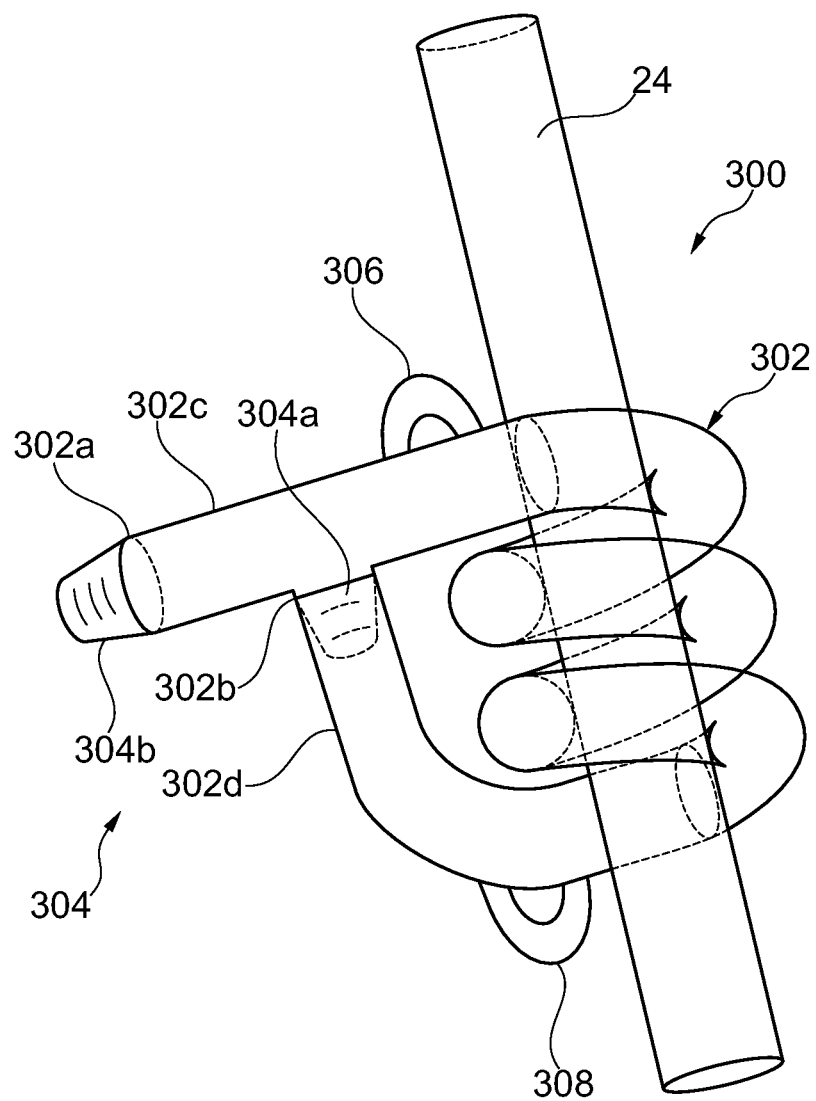
FIG. 4 is a diagram illustrating one embodiment of a cuff that includes a pre-shaped spiral tube having a connector that is built into the pre-shaped spiral tube.

FIG. 4 is a diagram illustrating one embodiment of a cuff 300 that includes a pre-shaped spiral tube 302 having a connector 304 that is built into the pre-shaped spiral tube 302. In some embodiments, the cuff 300 is similar to the cuff 22 (shown in FIG. 1).

The pre-shaped spiral tube 302 has a first end 302a and a second end 302b, where the connector 304 is formed into the pre-shaped spiral tube 302 at the first end 302a and a first end portion 302c of the pre-shaped spiral tube 302, which is adjacent the first end 302a. The connector 304 includes a first connector 304a and a second connector 304b. The first connector 304a is suitable for attachment to the second end 302b of the elastic tube 302, such that the second end 302b and a second end portion 302d of the elastic tube 302, which is adjacent the second end 302b, engage the first connector 304a to provide a snug, fluid tight fit. The second connector 304b is suitable for attachment to tubing, such as tubing 30 (shown in FIG. 1). In some embodiments, the cuff 300 includes eyelets 306 and 308.

In some embodiments, the cuff 300 is similar to the cuff 100 (shown in FIGS. 2A-2D) with the exception that instead of having a separate connector 104, the connector 304 is built into the pre-shaped spiral tube 302. In some embodiments, the cuff 300 is similar to the cuff 200 (shown in FIGS. 3A and 3B) with the exception that instead of having a separate connector 204, the connector 304 is built into the pre-shaped spiral tube 302. As embodiments of the cuffs 100 and 200 have been previously described in this disclosure, the descriptions will not be repeated here in relation to the cuff 300. Also, in some embodiments, the cuff 100 can have a built in connector, such as connector 304, instead of the connector 104, and in some embodiments, the cuff 200 can have a built in connector, such as connector 304, instead of the connector 204.

Figure 5:
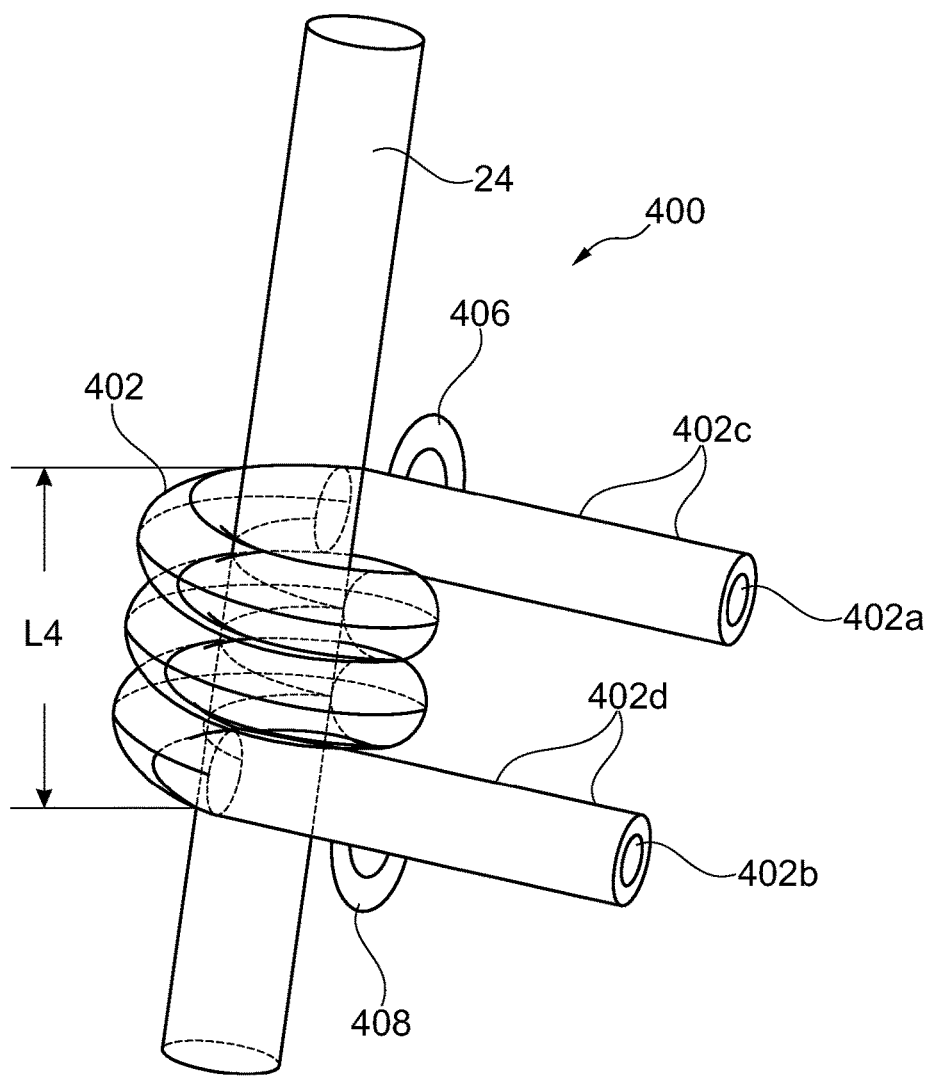
FIG. 5 is a diagram illustrating one embodiment of a cuff that includes a pre-shaped spiral tube wrapped around the urethra and having multiple coils situated side by side on the urethra.

FIG. 5 is a diagram illustrating one embodiment of a cuff 400 that includes a pre-shaped spiral tube 402 wrapped around the urethra 24 and having multiple coils situated side by side on the urethra 24. In some embodiments, the cuff 400 includes a separate connector (not shown in FIG. 5), and in some embodiments, the cuff 400 includes a built in connector (not shown in FIG. 5). In some embodiments, the cuff 400 is similar to the cuff 22 (shown in FIG. 1).

The pre-shaped spiral tube 402 has a first end 402a, a second end 402b, a first end portion 402c that is adjacent the first end 402a, and a second end portion 402d that is adjacent the second end 402b. In some embodiments, the pre-shaped spiral tube 402 includes eyelets 406 and 408 for securing and anchoring the pre-shaped spiral tube 402 to the tissue of the patient. The eyelets 406 and 408 can be situated at the end portions 402c and 402d, respectively, of the pre-shaped spiral tube 402.

The pre-shaped spiral tube 402 is sized to fit around the urethra 24. The pre-shaped spiral tube 402 is wrapped around the urethra 24 multiple times, such as 2 or 3 or more times, to form annular rings or coils around the urethra 24. The rings or coils of the pre-shaped spiral tube 402 can be stacked one on top of the other, such that the rings or coils are situated adjacent one another and touch or nearly touch each other, in at least one of the inflated and the deflated condition. The eyelets 406 and 408 can then be secured or tied to the tissue of the patient to anchor the pre-shaped spiral tube 402 in place and to prevent the coils of the pre-shaped spiral tube 402 from expanding and separating further apart along a length, such as the length L2, of the urethra 24. In some embodiments, the pre-shaped spiral tube 402 is wrapped around the urethra 24 for a length of up to 2 cm. In some embodiments, the pre-shaped spiral tube 402 is wrapped around the urethra 24 for a length of less than 1 cm.

In some embodiments, the cuff 400 is similar to the cuff 100 (shown in FIGS. 2A-2D). In some embodiments, the cuff 400 is similar to the cuff 200 (shown in FIGS. 3A and 3B). In some embodiments, the cuff 400 is similar to the cuff 300 (shown in FIG. 4). As embodiments of the cuffs 100, 200, and 300 have been previously described in this disclosure, the descriptions will not be repeated here in relation to the cuff 400.

Figure 6A:
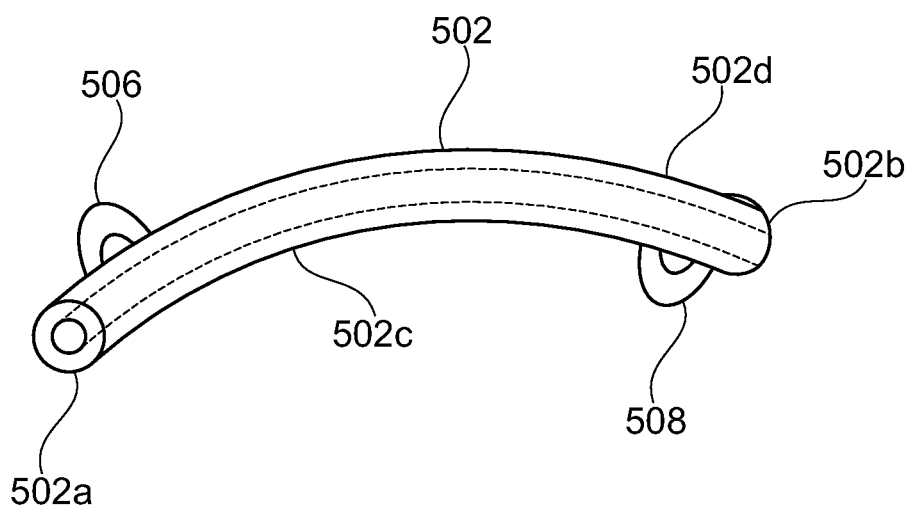
FIG. 6A is a diagram illustrating one embodiment of a kink resistant tube of a cuff.
Figure 6B:
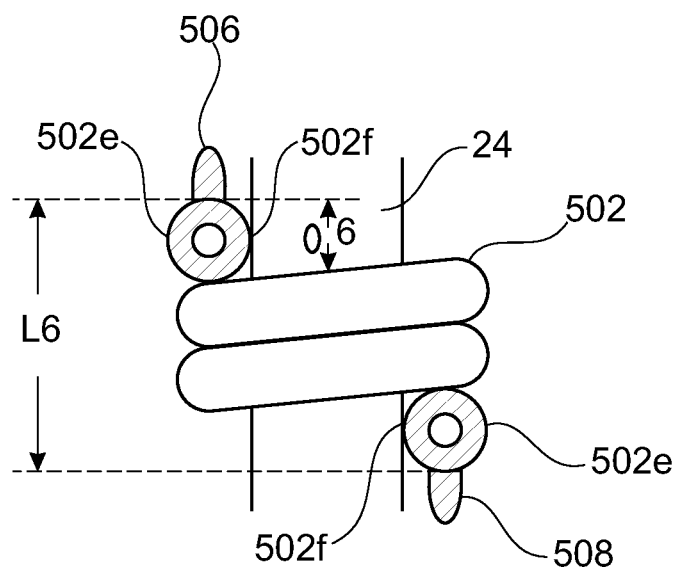
FIG. 6B is a diagram illustrating one embodiment of the kink resistant tube wrapped around the urethra.
Figure 6C:
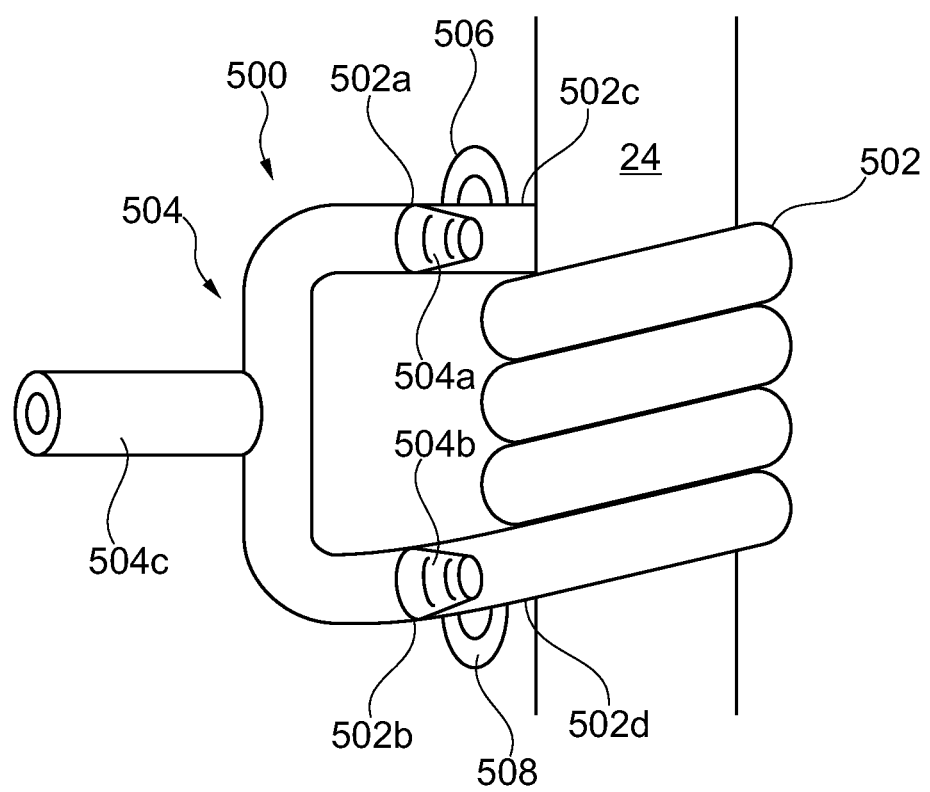
FIG. 6C is a diagram illustrating one embodiment of the cuff, which includes the kink resistant tube and the connector, on the urethra.

FIGS. 6A-6C are diagrams illustrating one embodiment of a cuff 500 that includes kink resistant tubing or a kink resistant tube 502 and a connector 504. In some embodiments, the cuff 500 has a built in connector that can be similar to the built in connector 304 (shown in FIG. 4), which is built into the kink resistant tube 502, instead of including the separate connector 504. In some embodiments, the cuff 500 is similar to the cuff 22 (shown in FIG. 1).

The kink resistant tube 502 is wrapped around the urethra 24 and the connector 504 is attached to the kink resistant tube 502. A control device, such as control device 26, is fluidically coupled to the connector 504 and to a reservoir, such as reservoir 28, to expand and contract the kink resistant tube 502 to coapt the urethra 24 for continence and open the urethra 24 for voiding. In some embodiments, the kink resistant tube 502 is wrapped around the urethra 24 at least one time. In some embodiments, the kink resistant tube 502 is wrapped around the urethra 24 at least two times, such as two and a half times.

FIG. 6A is a diagram illustrating one embodiment of the kink resistant tube 502. The kink resistant tube 502 has a first end 502a, a second end 502b, a first end portion 502c that is adjacent the first end 502a, and a second end portion 502d that is adjacent the second end 502b.

The kink resistant tube 502 fits around the urethra 24, such that the kink resistant tube 502 does not kink or wrinkle as it is wrapped around the urethra 24. The kink resistant tube 502 is made out of an elastic material, such that the kink resistant tube 502 expands upon being filled with fluid. In some embodiments, the kink resistant tube 502 is produced as a single wall extruded piece of tubing. In some embodiments, the kink resistant tube 502 includes a urethane elastomer. In some embodiments, the kink resistant tube 502 includes a urethane elastomer having a wall thickness of between 0.25 and 2 mm, such as a wall thickness of 0.75 mm. In some embodiments, the kink resistant tube 502 includes silicone. In some embodiments, the kink resistant tube 502 includes silicone having a wall thickness of between 1 and 2 mm.

In some embodiments, the kink resistant tube 502 includes eyelets 506 and 508 for securing and anchoring the kink resistant tube 502 to the tissue of the patient. The eyelets 506 and 508 can be situated at the end portions 502c and 502d, respectively, of the kink resistant tube 502. The eyelets 506 and 508 are secured or tied to the tissue of the patient to anchor the kink resistant tube 502 in place and to prevent the coils of the kink resistant tube 502 from expanding and separating further apart along a length L6 of the urethra 24 (shown in FIG. 6B).

FIG. 6B is a diagram illustrating one embodiment of the kink resistant tube 502 wrapped around the urethra 24. The kink resistant tube 502 is wrapped around the urethra 24 at least one time and, in some embodiments, multiple times, such as 2, 2½, or 3 or more times, to form annular rings or coils around the urethra 24. The kink resistant tube 502 is wrapped around the urethra 24 for the length L6 of the urethra 24. In this situation, the same force can be used with multiple coils as with a single coil to constrict the urethra 24, but the force is applied over an increased area of the urethra 24, such that pressure at points along the urethra 24 is decreased. The decreased pressure along the urethra 24 leads to less irritation and less eroding of the urethra 24 under the cuff 500. In some embodiments, the kink resistant tube 502 is wrapped around the urethra 24 for a length L6 of up to 2 cm. In some embodiments, the kink resistant tube 502 is wrapped around the urethra 24 for a length L6 of less than 1 cm.

The kink resistant tube 502 has a circular cross-section and, in some embodiments, the kink resistant tube 502 has a circular cross-section from the first end 502a to the second end 502b. The kink resistant tube 502 has an exterior surface 502e that is the outermost portion of the kink resistant tube 502 and an inner surface 502f that is provided to contact the urethra 24. The exterior surface 502e is opposite of or 180 degrees displaced from the inner surface 502f. In some embodiments, the kink resistant tube 502 has an outer diameter D6 of between 2 and 9 mm.

To put the kink resistant tube 502 around the urethra 24, one of the first and second ends 502a and 502b is slid behind the urethra 24 to emerge from the other side of the urethra 24. The selected end can then be repeatedly slid behind the urethra 24 to rotate or wrap the kink resistant tube 502 onto the urethra 24. After the kink resistant tube 502 has been wrapped around the urethra 24 multiple times, the kink resistant tube 502 is connected to the connector 504.

In some embodiments, the eyelets 506 and 508 are secured to the tissue of the patient. This prevents the kink resistant tube 502 from sliding up and down on the urethra 24 and ensures expansion of the kink resistant tube 502 on the urethra 24 without separating or further separating the coils of the kink resistant tube 502.

FIG. 6C is a diagram illustrating one embodiment of the cuff 500, including the kink resistant tube 502 and the connector 504, on the urethra 24.

The connector 504 includes a first connector 504a, a second connector 504b, and a third connector 504c. The first end 502a and the first end portion 502c of the kink resistant tube 502 engage the first connector 504a to provide a snug, fluid tight fit. The second end 502b and the second end portion 502d of the kink resistant tube 502 engage the second connector 504b to provide a snug, fluid tight fit. The third connector 504c is suitable for attachment to tubing, such as tubing 30 (shown in FIG. 1). In some embodiments, the cuff includes the eyelets 506 and 508.

In some embodiments of the cuff 500, the kink resistant tube 502 is deflated to contract the kink resistant tube 502 and open the urethra 24 for voiding, and inflated to expand the kink resistant tube 502 and coapt or close-off the urethra 24 to prevent incontinence. In operation, as described in reference to FIG. 1, a control device such as control device 26 and a fluid reservoir such as fluid reservoir 28 cooperate to move fluid from the fluid reservoir to the kink resistant tube 502 of the cuff 500. This expands the kink resistant tube 502 and pinches off or closes the urethra 24. At some time, the fluid is removed from the kink resistant tube 502, which relaxes or contracts the kink resistant tube 502 from around the urethra 24 to allow the urethra 24 to open for voiding. The control device and the fluid reservoir further cooperate to move fluid from the fluid reservoir to the kink resistant tube 502 to expand the kink resistant tube 502 and close-off the urethra 24 to prevent incontinence.

In some embodiments of the cuff 500, the kink resistant tube 502 is deflated and contracted to pinch or close-off the urethra 24 to prevent incontinence, and inflated and expanded to allow the urethra 24 to open for voiding. In operation, as described in reference to FIG. 1, a control device such as control device 26 and a fluid reservoir such as fluid reservoir 28 cooperate to move fluid from the fluid reservoir to the kink resistant tube 502 of the cuff 500. This expands the kink resistant tube 502 from around the urethra 24 and allows the urethra 24 to open for voiding. After some time, the fluid is removed from the kink resistant tube 502, which contracts the kink resistant tube 502 to tighten around the urethra 24 and to close-off the urethra 24 to prevent incontinence.

Figure 7:
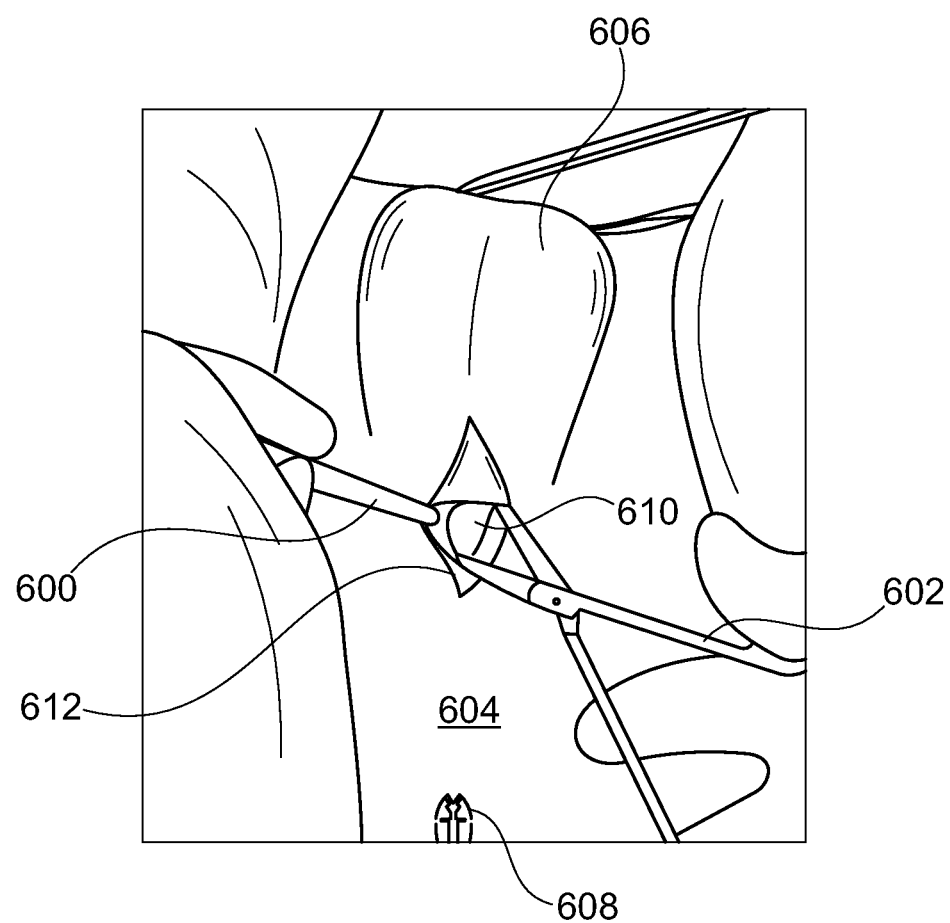
FIG. 7 is a schematic view of a scalpel and a dissection tool employed to dissect tissue through the perineum.

FIG. 7 is a schematic view of a scalpel 600 and a dissection tool 602 employed to dissect tissue through the perineum 604, which is situated between the scrotum 606 and the anus 608, to expose the bulbar urethra 610. An incision 612 is made through the perineum 604 to dissect the tissue.

Figure 8:
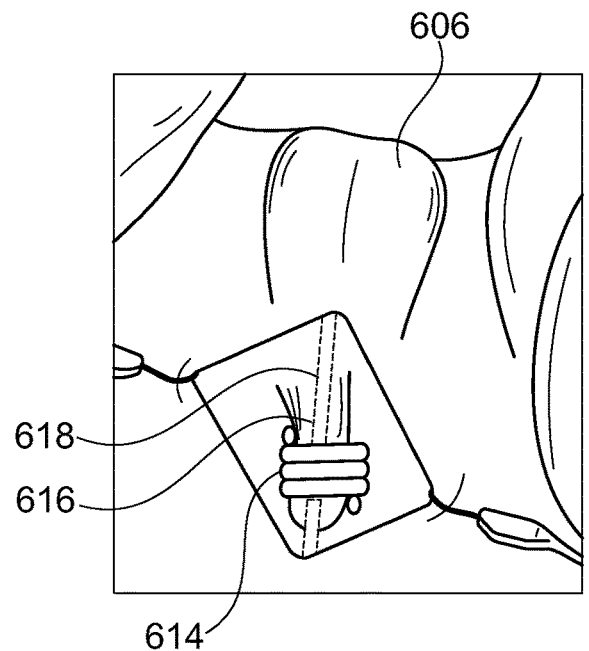
FIG. 8 is a schematic view of a cuff situated around the urethral bulb.

FIG. 8 is a schematic view of a cuff 614, such as one of the cuffs 22, 100, 200, 300, 400, and 500 situated around the urethral bulb 616. A urinary catheter 618 has been placed inside the bladder through the urethra to drain urine from the bladder, and the surgeon has dissected tissue away from and around the urethral bulb 616 for the suitable placement of the cuff 614.

Figure 9:
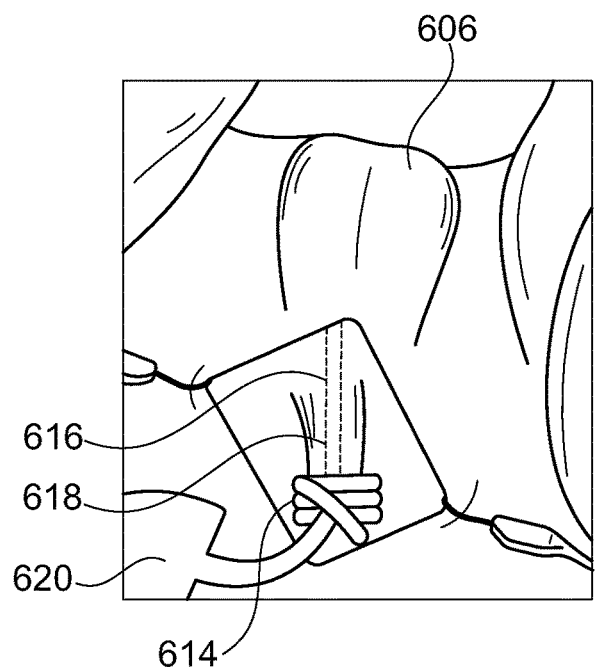
FIG. 9 is a schematic view of the cuff in place around the urethral bulb of the patient and connected to an AUS system.

FIG. 9 is a schematic view of the cuff 614 in place around the urethral bulb 616 of the patient and connected to an AUS system 620, similar to the AUS system 20 (shown in FIG. 1).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

The following is claimed:

1. An artificial urinary sphincter system, comprising:
   a reservoir to hold a fluid;
   a cuff that includes a pre-shaped spiral tube to be wrapped around a urethra having a first end portion and a second end portion and a fluid lumen extending between the first and second end portions;
   a connector having a fluid lumen coupled to the first end portion and the second end portion of the cuff such that fluid flows through the connector to the first and second end portions of the cuff; and
   a control device to be fluidically coupled to the reservoir and the connector and to regulate transfer of the fluid between the reservoir and the cuff through the fluid lumen of the connector, such that the cuff receives and dispatches the fluid to expand and contract the pre-shaped spiral tube and to coapt the urethra for continence and open the urethra for voiding, the control device being configured to move fluid from the cuff to open the urethra for voiding.

2. The system of claim 1, wherein the reservoir, the cuff, and the control device are configured to maintain an equilibrium pressure that closes the cuff around the urethra.

3. The system of claim 2, wherein the control device is configured to return to the equilibrium pressure subsequent to expansion of the cuff, and the cuff is configured to contract at the equilibrium pressure.

4. The system of claim 1, wherein the pre-shaped spiral tube includes at least two spirals to be situated around the urethra.

5. The system of claim 1, wherein the pre-shaped spiral tube includes a kink resistant tube.

6. The system of claim 1, wherein the pre-shaped spiral tube includes a single wall kink resistant tube.

7. The system of claim 1, wherein an elevated fluid pressure is maintained in the reservoir.

8. The system of claim 7, wherein the control device includes a pump to transfer the fluid from the cuff to the reservoir.

9. The system of claim 7, wherein the control device includes a valve to transfer the fluid from the reservoir to the cuff.

10. The system of claim 1, wherein the control device includes a pump to transfer the fluid from the reservoir to the cuff.

11. The system of claim 1, wherein the cuff includes a continuous flow lumen.

12. An artificial urinary sphincter system, comprising:
a reservoir to hold a fluid;
a cuff that includes a pre-shaped spiral tube to be wrapped around a urethra having a first end portion and a second end portion and a circular cross-section between the first end portion and the second end portion; and
a connector coupled to the first end portion and the second end portion of the cuff such that fluid flows through the connector to the first end portion and the second end portion of the cuff; and
a control device to be fluidically coupled to the reservoir and the connector and to regulate transfer of the fluid between the reservoir and the cuff through the connector to the first end portion and the second end portion of the cuff, such that the cuff receives and dispatches the fluid from the first end portion and the second end portion to expand and contract the pre-shaped spiral tube and to coapt the urethra for continence and open the urethra for voiding, the control device being configured to move fluid from the cuff to open the urethra for voiding.

13. An artificial urinary sphincter system, comprising:
a reservoir to hold a fluid;
a cuff that includes a pre-shaped spiral tube to be wrapped around a urethra having a first end portion and a second end portion with a fluid lumen extending between the first and second end portions;
a connector having a fluid lumen fluidically coupled to the first end portion and the second end portion of the cuff; and
a control device to be fluidically coupled to the reservoir and the connector and to regulate transfer of the fluid between the reservoir and the cuff through the connector, such that the cuff receives and dispatches the fluid from the first end portion and the second end portion to expand and contract the pre-shaped spiral tube and to coapt the urethra for continence and open the urethra for voiding.

* * * * *